United States Patent [19]

Ebert et al.

[11] Patent Number: 5,460,820
[45] Date of Patent: Oct. 24, 1995

[54] METHODS FOR PROVIDING TESTOSTERONE AND OPTIONALLY ESTROGEN REPLACEMENT THERAPY TO WOMEN

[75] Inventors: Charles D. Ebert, Salt Lake City; Dinesh C. Patel, Murray; Norman A. Mazer; Srinivasan Venkateshwaran, both of Salt Lake City, all of Utah

[73] Assignee: TheraTech, Inc., Salt Lake City, Utah

[21] Appl. No.: 99,923

[22] Filed: Aug. 3, 1993

[51] Int. Cl.⁶ .................................................. A61F 13/00
[52] U.S. Cl. ........................................... 424/449; 424/448
[58] Field of Search ................................... 424/448, 449

[56] References Cited

U.S. PATENT DOCUMENTS 5,023,084  6/1991  Chien ........................................ 424/448
5,152,997  10/1992  Ebert et al. ............................. 424/449

OTHER PUBLICATIONS

Urman et al., "Elevated serum testosterone, hirsutism, and virilism associated with combined and androgen–estrogen hormone replacement therapy" *Obstetrics & Gynecology* (1991) 77:595–598.

Sherwin, B. B., et al., "Sex steroids and affect in the surgical menopause: A double blind, cross–over study" *Psychoneuroendocrinology* (1985) 10(3):325≧335.

Sherwin, B. B., et al., "Androgen enhances sexual motivation in females: A prospective, crossover study of sex steroid administration in the surgical menopause" *Psychosomatic Medicine* (1985) 47(4):339–351.

Sherwin, B. B., et al., "Differential symptom response to parenteral estrogen and/or androgen administration in the surgical menopause" *American Journal of Obstetrics and Gynecology* (1985) 151(2):153–160.

Yu, J–W., et al., "Transdermal dual controlled delivery of testosterone and estradiol: (I) Impact of system design" *Drug Develoment and Industrial Pharmacy* (1991) 17(14):1883–1904.

Yu, J–W., et al., "Transdermal dual controlled delivery of testosterone and estradiol: (II) Enhanced skin permeability and membrane–moderated delivery" *Drug Development and Industrial Pharmacy* (1991) 17(14):1905–1930.

Primary Examiner—D. Gabrielle Phelan
Attorney, Agent, or Firm—Morrison & Foerster

[57] ABSTRACT

A method of providing testosterone replacement therapy to a woman in need of such therapy comprising applying a testosterone-delivering patch to the skin of said woman which patch transdermally delivers 50 to 500 µg/day of testosterone to the woman.

4 Claims, 1 Drawing Sheet

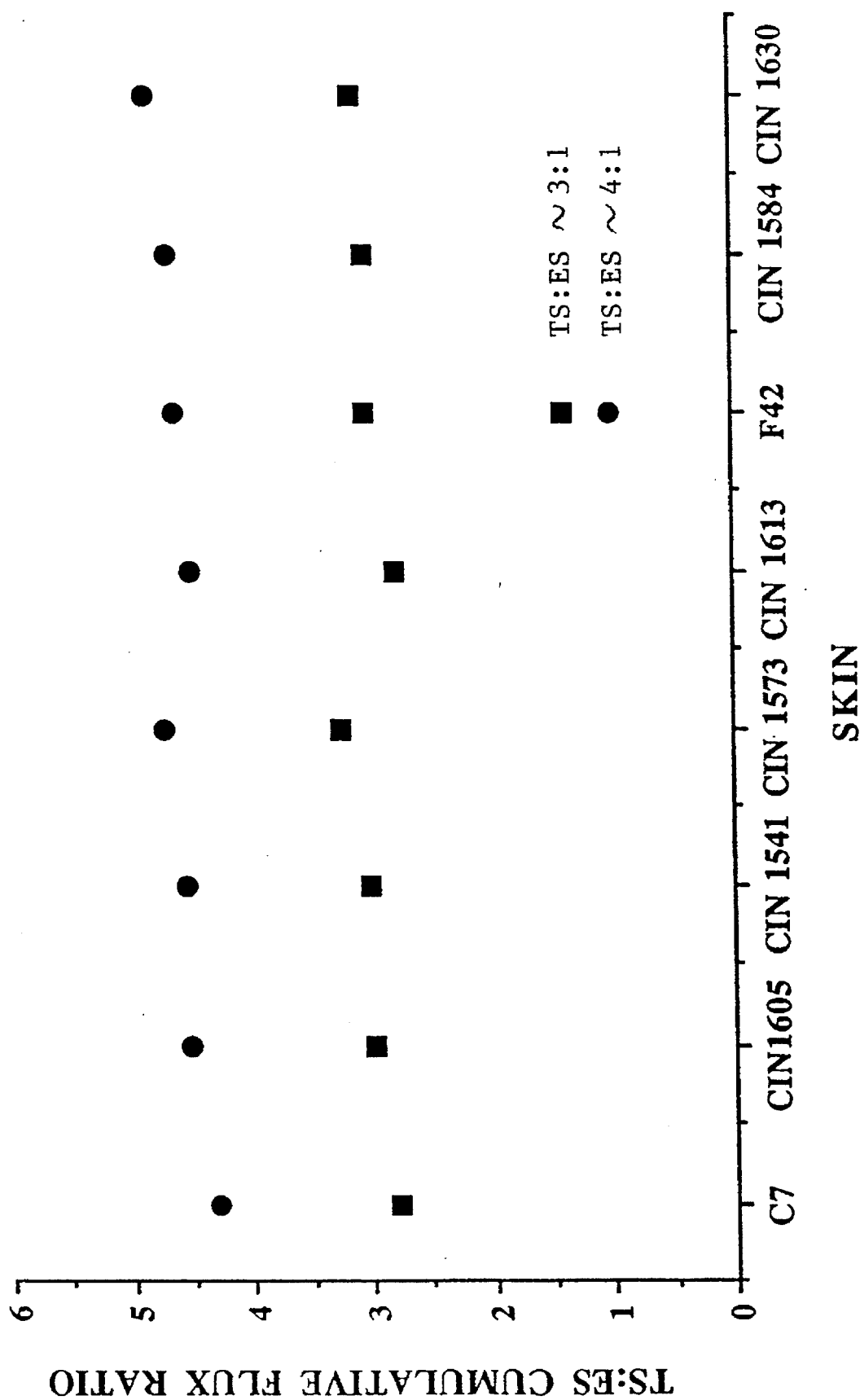

METHODS FOR PROVIDING TESTOSTERONE AND OPTIONALLY ESTROGEN REPLACEMENT THERAPY TO WOMEN

TECHNICAL FIELD

This invention is in the field of transdermal drug delivery. More particularly, it is directed to skin patches and methods for providing transdermal delivery of testosterone and optionally estrogens to women.

BACKGROUND

Estrogens are commonly used in hormone replacement therapy for the treatment of post-menopausal symptoms and osteoporosis. Many women, however, continue to experience symptoms after estrogen monotherapy. The beneficial effects of androgens on the post-menopausal woman's physical and emotional well-being are only recently being recognized. Several clinical studies have established the basis of combined estrogen-androgen therapy. In a series of double-blind, controlled studies at McGill University, it was noted that patients on estrogen-androgen combination therapy had higher daily scores of well-being, energy level, and quality of sleep than patients on estrogen replacement therapy (ERT) alone. The authors also reported a beneficial effect of estrogen-androgen therapy on sexual function, and no adverse effects on lipids.

Androgens are the hormones of choice in helping restore lost sex drive, although estrogens alone may help some women. Several reports in the literature establish the beneficial effects of androgen therapy on sexual function. This is particularly important in younger, surgically post-menopausal women, who have increased motivational aspect of sexual behavior (such as desire and arousal) when treated with parenteral androgen, either alone or in combination with an estrogen, compared to estrogen alone or placebo. Justification for the addition of androgens to ERT for the prevention of osteoporosis is also found in the literature.

While the benefits of adding an androgen to an ERT regimen are well established, the dosage forms available for androgen therapy or estrogen-androgen combination therapy leave much to be desired. In particular, none of these modalities can produce serum testosterone levels that remain within normal physiological range on a daily basis. The androgens most available for clinical use are not typically the native testosterone; synthetic androgens are commonly used (methyl testosterone, for example which is known to be hepatotoxic). Native testosterone is available as implantable pellets; however this system requires an invasive administration and does not produce a stable physiological hormonal state. Injectable testosterone esters such as testosterone propionate and the long-acting testosterone enanthate produce marked supraphysiological fluctuations in hormone levels. The non- and supraphysiological nature of the current androgen replacement products are responsible for the signs and symptoms of excess androgen effect frequently seen with their use. These include virilizing symptoms such as hirsutism, male pattern baldness, voice lowering and clitoromegaly; disturbances in ovulation and menstrual function; acne and oily skin; and breast tenderness, fluid retention, irritability and depression. These problems are also present with estrogen-androgen products currently on the market. A modality producing physiological levels of testosterone and its metabolites, with or without estrogen, would have significant therapeutic benefits over existing androgen replacement products.

Many articles and patents have suggested or reported transdermal administration of testosterone. In general, these publications have focused on providing testosterone therapy to men to treat conditions such as male hypogonadism, anemia, and male osteoporosis. Much of this literature concludes that testosterone, without some form of permeation enhancement, does not pass through non-scrotal skin at practical fluxes. Most recently, U.S. Pat. No. 5,152,997 describes the transdermal administration of testosterone to males through non-scrotal skin under conditions (subsaturation concentrations of testosterone in the skin patch; coadministration of skin permeation enhancers) that provide practical flux levels. This literature is virtually silent on the subject of providing testosterone or combined testosterone/estrogen replacement therapy to women transdermally.

DISCLOSURE OF THE INVENTION

One aspect of this invention is a method of providing testosterone replacement therapy to a woman in need of such therapy comprising administering testosterone transdermally to the woman in an amount that provides blood levels of testosterone in the woman that correspond substantially to endogenous blood levels of testosterone in healthy young adult women.

Another aspect of the invention is a skin patch for providing testosterone replacement therapy transdermally to a woman in need of such therapy comprising a laminated composite of:

(a) a backing layer; and (b) a matrix layer comprising a solution of testosterone in a polymeric carrier, said matrix layer providing a sufficient daily dose of testosterone to provide said therapy.

Still another aspect of the invention is a method of providing combined testosterone and estrogen replacement therapy to a woman in need of such therapy comprising coadministering testosterone and estrogen transdermally to the woman in respective amounts that provide blood levels of testosterone and estrogen in the woman that correspond substantially to endogenous blood levels of testosterone and estrogen in healthy young adult women.

Yet another aspect of the invention is a skin patch for providing testosterone and estrogen replacement therapy transdermally to a woman in need of such therapy comprising:

(a) a backing layer;

(b) a testosterone-and-estrogen-containing reservoir layer that is adapted to be in diffusional communication with the skin of the woman and to transmit therapeutically effective amounts of testosterone and estrogen through the skin of the woman.

BRIEF DESCRIPTION OF THE DRAWINGS

The drawing is a graph of data described in Example 2, infra.

MODES FOR CARRYING OUT THE INVENTION

As used herein, the word "estrogen" intends 17β-estradiol; esters thereof such as estradiol-3,17-diacetate, estradiol-3-acetate, estradiol-17-acetate, estradiol-3,17-divalerate, estradiol-3-valerate, estradiol-17-valerate, and the corresponding pivalate, propionate, cypionate, benzoate, and like esters; ethinyl estradiol, estrone, and other estrogenic steroids and derivatives thereof that are suitable for transdermal administration.

As used herein the term "testosterone replacement therapy" intends the transdermal administration to a woman of all or a portion of the testosterone that is normally produced by a healthy young adult woman. In this regard, in healthy adult women approximately 50% of the testosterone is produced by each of the ovaries and the adrenal glands. Thus, in most instances this therapy will be provided to women who have undergone bilateral oopherectomy, post-menopausal with diminished androgen production, and women with diminished adrenal androgen production (e.g., Addison's disease). This latter group also includes women who receive high dose corticosteroid therapy that can secondarily suppress adrenal androgen production.

As used herein the term "flux" intends the rate of transfer of hormone across skin as measured by the method of Merritt and Cooper (J Controlled Release (1984) 1:161).

The term "endogenous serum levels" as used herein intends the serum levels of testosterone or estradiol, as the case may be, that are normally found in healthy young adult women. In the case of testosterone this value is about 15 to 80 ng/mL; whereas for estradiol it is about 25 to 200 pg/mL. In the case of derivatives of testosterone or estradiol, amounts that provide equivalent androgenic or estrogenic activity, as the case may be, to the natural hormones are intended. The term "corresponds substantially" intends a permitted standard deviation of $\geq 100\%$ in the case of both testosterone and estradiol.

The term "diffusional communication" intends that when the invention patch is placed on the skin/mucosa of a woman, there is a direct or indirect diffusional pathway by which the testosterone and optionally estrogen can migrate from the hormone-containing element(s) of the patch to the skin/mucosa of the wearer.

The daily dose of testosterone that will normally be required to provide replacement therapy to females is in the range of 50 to 500 µg/day, more usually 100 to 300 µg/day. Correspondingly, the daily dose of 17β-estradiol will normally be in the range of 25 to 200 µg/day, more usually 50 to 100 µg/day. Thus, for patches in the 5 to 30 $cm^2$ diffusional area range, the flux of testosterone will be in the range of 1.7 to 100 µg/$cm^2$/day, more usually 3.3 to 60 µg/$cm^2$/day whereas the flux of estradiol will usually be in the range of 0.8 to 40 µg/$cm^2$/day, more usually 1.7 to 20 µg/$cm^2$/day.

The patches that are used to provide such daily doses of testosterone and optionally estradiol may be of the matrix or container type. In matrix-type patches, the hormone(s) is/are homogeneously blended in a solid or semisolid polymer carrier together with other additives (e.g., permeation enhancers, plasticizers, viscosity reducing agent, and the like). In container-type devices, the hormones are typically dissolved or suspended in liquid or semi-solid vehicles, and confined within a pouch or space between a backing and an underlying membrane which is permeable to the hormone(s). The general structure and fabrication of both matrix and container-type patches are well known in the art.

A preferred patch for administering testosterone or testosterone/estrogen in accordance with this invention is a matrix-type patch which comprises an occlusive backing that is impermeable to the testosterone/estrogen and defines the face or top surface of the patch and a solid or semisolid matrix layer comprised of a homogeneous blend of the hormone(s), a polymeric carrier, and one or more skin permeation enhancers.

The particular chemistry of the polymeric carrier is not critical. Rather, the diffusion coefficient of the hormone(s) in the carrier and the solubilities of the hormone(s) in the carrier are important. In this regard the diffusion coefficient of the hormone(s) in the carrier will usually be between $10^{-4}$ and $10^{-12}$ $cm^2$/sec, more usually $10^{-5}$ and $10^{-8}$ $cm^2$/sec. Correspondingly, the solubilities of the hormones in the carrier will usually be in the range of 1 to 200 mg/$cm^3$, more usually 10 to 100 mg/$cm^3$. The amount of testosterone and optionally estrogen in the carrier will be sufficient to provide the required daily dose of hormone(s) over the intended wearing time. The hormone(s) are preferably present in the carrier below their saturation concentrations to avoid crystallization. The patches will be typically designed to be worn for 1 to 14 days, more usually 1 to 7 days. Accordingly, the amount of testosterone in the carrier will normally be between 0.1 to 30 mg, more usually 1 to 10 mg and the amount of estrogen, when present, will usually be between 0.1 and 10 mg, more usually 0.5 and 5 mg. The thickness of the matrix layer will normally be 0.01 to 1 mm, more usually 0.025 to 0.25 mm. The area of the patch in diffusional contact with the skin will usually be between 1 and 150 $cm^2$, more usually 5 and 40 $cm^2$. The polymeric carrier may be adhesive or nonadhesive. When it is a pressure sensitive adhesive the basal surface of the matrix layer may be used to affix the patch to the skin. When it is not, other means such as an underlying adhesive layer, a peripheral adhesive layer, an adhesive overlay, or straps may be used to affix the patch to the skin.

Examples, without limitation, of specific polymers that may be used as the carrier are polyacrylates, polymethacrylates, natural and synthetic rubbers, silicone rubbers and elastomers, polyolefins, vinyl copolymers, urethanes, nylons, polyesters, polyethers, and the like.

The skin permeation enhancer(s) that are included in the matrix enhance the level of skin flux of the hormone(s). Examples, without limitation, of skin permeation enhancers that may be used are those described or referred to in U.S. Pat. Nos. 5,122,383 and 5,152,997, the disclosures of which as they relate to skin permeation enhancers, are incorporated by reference. The enhancer will usually constitute 1 to 20 wt % of the matrix, more usually 5 to 15 wt % of the matrix.

The patches of the invention may be manufactured by conventional techniques used in transdermal drug delivery device art. For instance, the hormone(s), carrier, and enhancer(s) may be mixed in the desired proportions to form a homogeneous mixture and cast or otherwise applied to a backing layer, by lamination to a release liner layer.

The following examples further illustrate the invention. These examples are not intended to limit the invention in any manner. Unless indicated otherwise percentages and proportions are by weight.

EXAMPLES

Example 1

Testosterone (TS) was obtained from the Upjohn Company. Sorbitan monooleate (Arlacel 80) was obtained from ICI Americas. Polyacrylate adhesive (Durotak 80-1196) was obtained from National Starch and Chemical Company. Release liner (polyester, S242M) was obtained from Release Technologies, Inc. and polyethylene backing film (Cotran 9720) from 3M corporation.

The solid content of the adhesive was determined by weighing a small amount of the adhesive solution in a pre-weighed aluminum dish. The solvent was evaporated by overnight drying in a convection oven maintained at 70° C. and the % solid adhesive content determined based upon the weight of the dried adhesive.

Known amounts of the adhesive solution were weighed into glass bottles. From the weight of the adhesive solution and the percent solid adhesive content, the amount of adhesive in the solution was calculated. Appropriate quantities of testosterone and sorbitan monooleate were added to the adhesive solution to yield a dried film composition in which the adhesive, testosterone, sorbitan monooleate were in a weight ratio of 83:2:15. The glass bottle was then tightly capped, sealed with parafilm, and rotated overnight until all ingredients had completely dissolved and the solution was visually clear.

About 8 ml of the adhesive/testosterone/ sorbitan monooleate mixture was then dispensed on a release liner, and cast with a 250 micron gap casting knife. This cast was dried in a convention oven at 70° C. for 15 minutes to yield a dry film thickness of approximately 60 microns. The backing film was then laminated onto this adhesive film using a rubber roller. This matrix laminate was used to conduct in vitro skin flux studies.

Similar laminates were made using other enhancers (glyceryl monooleate, methyl laurate, ascorbyl stearate, and ascorbyl palmitate) and different amounts of enhancer (5%–15% by weight), and different TS loadings at 15% enhancer loading.

The in vitro skin flux studies were conducted by the general method of Merritt and Cooper, supra, using modified Franz diffusion cells. Heat separated human epidermal membrane was cut into rectangular strips. The matrix was also cut into corresponding rectangular strips. After the release liner was peeled and discarded, the matrix was laminated onto the stratum corneum surface of the epidermal membrane. The skin-matrix sandwich was then cut into smaller pieces for loading onto the diffusion cells. Each piece of the skin matrix sandwich was loaded between the donor and receiver compartments of a diffusion cell, with the epidermal side facing the receiver compartment, and clamped in place. The receiver compartment was then filled with 0.02% sodium azide solution. The solubility of the testosterone in this medium is adequate to ensure sink conditions throughout the experiment. The cell was then placed in a circulating water bath calibrated to maintain the skin surface temperature at 32°±1° C.

At predetermined intervals, the entire contents of the receiver compartment was collected for TS quantitation, and the receiver compartment was refilled with fresh receptor medium, taking care to eliminate any air bubbles at the skin/solution interface. The cumulative amount of TS permeated per unit area at any time t ($Q_t$, $\mu g/cm^2$) was determined as follows:

$$Q_t = \sum_{n=0}^{t} (C_n * V)/A$$

where $C_n$ is the concentration (μg/ml) of drug in the receiver sample for the corresponding sample time, V is the volume of fluid in the receiver chamber (~6.3 cm³), and A is the diffusional area of the cell (0.64 cm²). The slope of the best fit line to the $Q_t$ vs. t plot gives the steady state flux ($J_{ss}$, μg/cm²/h); the intercept of this line on the time axis gives the lag time ($t_L$, h).

Reverse-phase HPLC was used to determine the concentration of TS in samples from in vitro. The HPLC methodology is summarized below.

Mobile Phase: 47/53 % (v/v) Acetonitrile/H₂O
Flow Rate: 1.0 Ml/min
Column: Partisphere C18, 10 cm (Whatman)
Injection Volume: 50 μL
Wave Length: 245 nm
Retention Time: 4.5–4.8 min
Run Time: 6 min From these studies a twice-a-week (i.e., to be worn ≈3–4 days) prototype testosterone patch was designed. The matrix formulation of the prototype patch is Durotak 80-1196 (83%)/TS (2%)/Arlacel 80 (15%). The coating weight of the matrix is 91±9.1 mg; the size is 15 cm², and the daily dose is approximately 150 μg/day.

Example 2

Estradiol (ES) was obtained from Diosynth, Inc. Other materials were obtained as described in Example 1.

Based on the studies of Example 1 two patches which coadminister TS and ES were made. One was designed to have a TS:ES flux of 4:1; the other a 3:1 flux ratio. The matrix composition of the 4:1 patch was Durotak 80-1196 (80.5%)/Arlacel 80 (15%)/ES (1.5%)/TS (3%). The matrix composition of the 3:1 patch was Durotak 80-1196 (81.5%)/Arlacel 80 (15%)/ES (1.5%)/TS (2%). Other patch components were as in Example 1.

Flux studies were carried out on these patches as in Example 1. The drawing is a plot of the data from these studies. Specifically the drawing shows the TS:ES flux ratio for each of 8 skin samples. Based on these studies a 3:1 ratio 10–20 cm² patch targeted to deliver ≈150 μg/day TS and 50 μg/day ES was developed.

Modifications of the above described modes for carrying out the invention that are obvious to those of skill in the fields of pharmaceuticals, hormone replacement therapy, transdermal drug delivery and related arts are intended to be within the scope of the following claims.

We claim:

1. A method of providing testosterone replacement therapy to a woman in need of such therapy comprising administering 50 to 500 μg/day of testosterone transdermally to the woman thereby causing blood level of testosterone in the woman to be about 15 to 80 ng/mL said administration being via a skin patch comprising a backing layer and a testosterone-containing layer that is in diffusional communication with the skin of the woman.

2. The method of claim 1 wherein 100 to 300 μg/day of testosterone is administered transdermally to the woman.

3. A method of providing combined testosterone and estrogen replacement therapy to a woman in need of such therapy comprising coadministering 50 to 500 μg/day of testosterone and estrogen in an amount equivalent to 25 to 200 μg/day of 17β-estradiol transdermally to the woman thereby causing the blood level of testosterone in the woman to be 15 to 80 ng/mL and the amount of estrogen to be an amount that provides equivalent estrogenic activity to a level of 25 to 200 pg/mL of 17β-estradiol said coadministration being via a skin patch comprising a backing layer and a testosterone-and estrogen-containing layer that is in diffusional communication with the skin of the woman.

4. The method of claim 3 wherein the amount of testosterone administered is 100 to 300 μg/day and the estrogen is 17β-estradiol and the amount of estrogen administered is 50 to 100 μg/day.

* * * * *

UNITED STATES PATENT AND TRADEMARK OFFICE
CERTIFICATE OF CORRECTION

PATENT NO. : 5,460,820
DATED : October 24, 1995
INVENTOR(S) : C. Ebert; D. Patel; N. Mazer; S. Venkateshwaran It is certified that error appears in the above-indentified patent and that said Letters Patent is hereby corrected as shown below:

Col. 3, line 23, "ng/mL," should be replaced with --ng/dL--.

Col. 6, line 44, "ng/mL," should be replaced with --ng/dL--.

Col. 6, line 56, "ng/mL," should be replaced with --ng/dL--.

Signed and Sealed this

Seventeenth Day of October, 2000

Q. TODD DICKINSON

*Attest:*

*Attesting Officer*      *Director of Patents and Trademarks*

REEXAMINATION CERTIFICATE (3827th)

United States Patent [19]
Ebert et al.

[11] B1 5,460,820
[45] Certificate Issued Aug. 3, 1999

[54] METHOD FOR PROVIDING TESTOSTERONE AND OPTIONALLY ESTROGEN REPLACEMENT THERAPY TO WOMEN

[75] Inventors: Charles D. Ebert, Salt Lake City; Dinesh C. Patel, Murray; Norman A. Mazer; Srinivasan Venkateshwaran, both of Salt Lake City, all of Utah

[73] Assignee: TheraTech, Inc., Salt Lake City, Utah

Reexamination Request:
No. 90/005,073, Aug. 13, 1998

Reexamination Certificate for:
Patent No.: 5,460,820
Issued: Oct. 24, 1995
Appl. No.: 08/099,923
Filed: Aug. 3, 1993

Certificate of Correction issued Oct. 24, 1995.

[51] Int. Cl.[6] ...................................................... A61F 13/00
[52] U.S. Cl. ........................................... 424/449; 424/448
[58] Field of Search ..................................... 424/448, 449

[56] References Cited

U.S. PATENT DOCUMENTS

| | | |
|---|---|---|
| 3,731,683 | 5/1973 | Zaffaroni . |
| 3,797,494 | 3/1974 | Zaffaroni . |
| 4,264,575 | 4/1981 | Zimmerman et al. . |
| 4,336,243 | 6/1982 | Sanvordeker et al. . |
| 4,704,282 | 11/1987 | Campbell et al. . |
| 4,762,717 | 8/1988 | Crowley, Jr. . |
| 5,122,382 | 6/1992 | Gale ........................................ 424/449 |
| 5,152,997 | 10/1992 | Ebert ...................................... 424/449 |
| 5,340,584 | 8/1994 | Spicer et al. . |
| 5,340,585 | 8/1994 | Pike et al. . |
| 5,340,586 | 8/1994 | Pike et al. . |

OTHER PUBLICATIONS

J. Bancroft et al., "Mood, Sexuality, Hormones, and the Menstrual Cycle. III. Sexuality and the Role of Androgens," *Psychosomatic Medicine*, 45(6): 509–516 (1983).

D. H. Barlow et al., "Long–Term Hormone Implant Therapy—Hormonal and Clinical Effects," *Obstetrics & Gynecology*, 67(3): 321–325 (1986).

J. R. Buchanan et al., "Effect of Excess Endogenous Androgens on Bone Density in Young Women," *J. Clinical Endocrinology and Metabolism*, 67(5): 937–943 (1988).

H. G. Burger et al., "The Management of Persistent Menopausal Symptons with Oestradiol—Testosterone Implants: Clinical, Lipid and Hormonal Results," *Maturitas*, 6: 351–358 (1984).

C. Campagnoli et al., "Long–term Hormmone Replacement Treatment in Menopause: New Choices, Old Apprehensions, Recent Findings," *Maturitas*, 18: 21–46 (1993).

T. Garnett et al., "The Effects of Plasma Estradiol Levels on Increases in Vertebral and Femoral Bone Density Following Therapy with Estradiol and Estradiol with Testosterone Implants," *Obstetrics & Gynecology*, 79(6): 968–972, (1992).

M. M. Gelfand et al., "Endometrial Response to Estrogen–Androgen Stimulation," *Menopause: Evaluation, Treatment, and Health Concerns*, Alan R. Liss, Inc., pp. 29–40, 1989.

R. B. Greenblatt et al., "Evaluation of an Estrogen, Androgen, Estrogen–Androgen Combination, and a Placebo in the Treatment of the Menopause," *J. Clinical Endocrinology*, 10: 1547–1558, (1950).

K. Häkkinen and A. Pakarinen, "Muscle Strength and Serum Testosterone, Cortisol and SHBG Concentrations in Middle–Aged and Elderly Men and Women," *Acta Physiol Scand*, 148: 199–207, (1993).

(List continued on next page.)

*Primary Examiner*—D. Gabrielle Brouillette

[57] ABSTRACT

A method of providing testosterone replacement therapy to a woman in need of such therapy comprising applying a testosterone-delivering patch to the skin of said woman which patch transdermally delivers 50 to 500 μg/day of testosterone to the woman.

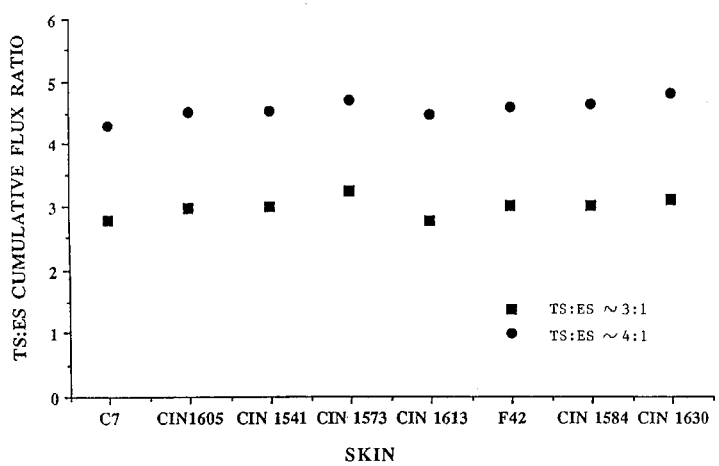

OTHER PUBLICATIONS

L. R. Hickok et al., "A Comparison of Esterified Estrogens with and without Methyltestosterone: Effects on Endometrial Histology and Serum Lipoproteins in Postmenopausal Women," *Obstetrics & Gynecology*, 82(6): 919–924, (1993).

C. L. Hughes et al., "Reproductive Hormone Levels in Gynecologic Oncology Patients Undergoing Surgical Castration after Spontaneous Menopause," *Gynecologic Oncology*, 40: 42–45, (1991).

H. L. Judd, et al., "Effect of Oophorectomy on Circulating Testosterone and Androstenedione Levels in Patients with Endometrial Cancer," *Am. J. Obstet. Gynecol.*, 118(6): 793–798, (1974).

E. Kapetanakis et al., "Endocrine and Clinical Effects of Estradiol and Testosterone Pellets used in Long–Term Replacement Therapy," *Int. J. Gynaecol. Obstet.*, 20: 387–399, (1982).

C. Kasperk et al., "Studies of the Mechanism by which Androgens Enhance Mitogenesis and Differentiation in Bone Cells," *J. Clinical Endocrinology and Metabolism*, 71(5): 1322–1329, (1990).

H. S. Kupperman et al., "Contemporary Therapy of the Menopausal Syndrome," *JAMA*, 171(12): 1627–1637, (1959).

C. Longcope et al., "Steroid and Gonadotropin Levels in Women During the Peri–Menopausal Years," *Maturitas*, 8: 189–196, (1986).

M. S. Marsh and M. I. Whitehead, "The Practicalities of Hormone Replacement Therapy," *Baillier's Clinical Endocrinology and Metabolism*, 7(1): 183–195. (1993).

R. S. Mathur et al., "The Effect of Estrogen Treatment on Plasma Concentrations of Steroid Hormones, Gonadotropins, Prolactin and Sex Hromone–Binding Globulin in Post–Menopausal Women," *Maturitas*, 7: 129–133, (1985).

L. S. Myers et al., "Effects of Estrogen, Androgen, and Progestin on Sexual Psychophysiology and Behavior in Postmenopausal Women," *J. Clinical Endocrinology and Metabolism*, 70(4): 1124–1131, (1990).

M. Passeri et al., "Effects of Nandrolone Decanoate on Bone Mass in Established Osteoporosis," *Maturitas*, 17: 211–219, (1993).

B. L. Riggs et al., "Short– and Long–Term Effects of Estrogen and Synthetic Anabolic Hormone in Postmenopausal Osteoporosis," *J. Clinical Investigation*, 51: 1659–1663, (1972).

M. Savvas et al., "Skeletal Effects of Oral Oestrogen Compared with Subcutaneous Oestrogen and Testosterone in Postmenopausal Women," *British Medical Journal*, 297: 331–333, (1988).

M. Savvas et al., "Increase in Bone Mass After One Year of Percutaneous Oestradiol and Testosterone Implants in Post–Menopausal Women who have Previously Received Long–Term Oral Oestrogens," *British Journal of Obstetrics and Gynaecology*, 99: 757–760, (1992).

B. B. Sherwin and M. M. Gelfand, "Effects of Parenteral Administration of Estrogen and Androgen on Plasma Hormone Levels and Hot Flushes in the Surgical Menopause," *Am. J. Obstet. Gynecol.*, 148(5): 552–557, (1984).

B. B. Sherwin and M. M. Gelfand, "Differential Symptom Response to Parenteral Estrogen and/or Androgen Administration in the Surgical Menopause," *American Journal of Obstetrics and Gynecology*, 151(2): 153–160, (1985).

B. B. Sherwin and M. M. Gelfand, "The Role of Androgen in the Maintenance of Sexual Functioning in Oophorectomized Women," *Psychosomatic Medicine*, 49: 397–409, (1987).

B. B. Sherwin, "Estrogen and/or Androgen Replacement Therapy and Cognitive Functioning in Surgically Menopausal Women," *Psychoneuroendocrinology*, 13(4): 345–357, (1988).

B. B. Sherwin, "Affective Changes with Estrogen and Androgen Replacement Therapy in Surgically Menopausal Women," *J. Affective Disorders*, 14: 177–187, (1988).

K. K. Steinberg et al., "Sex Steroids and Bone Density in Premenopausal and Perimenopausal Women," *J. Clinical Endocrinology and Metabolism*, 69(3): 533–539, (1989).

J. Studd et al., "The Relationship Between Plasma Estradiol and the Increase in Bone Density in Postmenopausal Women After Treatment with Subcutaneous Hormone Implants," *Am. J. Obstet. Gynecol.*, 163(5): 1474–1479, (1990).

M. H. Thom et al., "Hormonal Profiles in Postmenopausal Women After Therapy with Subcutaneous Implants," *British Journal of Obstetrics and Gynaecology*, 88: 426–433, (1981).

L. Weinstein, "Hormonal Therapy in the Patient with Surgical Menopause," *Obstetrics & Gynecology*, 75(4): 47S–52S, (1990).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 2 is confirmed.

Claim 3 is determined to be patentable as amended.

Claim 4, dependent on an amended claim, is determined to be patentable.

3. A method of providing combined testosterone and estrogen replacement therapy to a woman in need of such therapy comprising coadministering 50 to 500 µg/day of testosterone and estrogen in an amount equivalent to 25 to 200 µg/day of 17β-estradiol transdermally to the woman thereby causing the blood level of testosterone in the woman to be 15 to 80 ng/dL and the amount of estrogen to be an amount that provides equivalent estrogenic activity to a level of 25 to 200 pg/mL of 17β-estradiol said coadministration being via a skin patch comprising a backing layer and a testosterone-and estrogen-containing layer *in which the testosterone and estrogen are homogeneously blended* that is in diffusional communication with the skin of the woman.

\* \* \* \* \*